United States Patent
Kramer et al.

(10) Patent No.: US 7,129,087 B2
(45) Date of Patent: Oct. 31, 2006

(54) OLIGONUCLEOTIDE-FACILITATED COALESCENCE

(75) Inventors: Fred R. Kramer, Riverdale, NY (US); Osama A. Alsmadi, Guilford, CT (US); Sanjay Tyagi, New York, NY (US)

(73) Assignee: The Public Health Research Institute of the City of New York, Inc., Newark, NJ (US)

( * ) Notice: Subject to any disclaimer, the term of this patent is extended or adjusted under 35 U.S.C. 154(b) by 264 days.

(21) Appl. No.: 10/398,833

(22) PCT Filed: Oct. 11, 2001

(86) PCT No.: PCT/US01/42658
§ 371 (c)(1), (2), (4) Date: Aug. 12, 2003

(87) PCT Pub. No.: WO02/33045
PCT Pub. Date: Apr. 25, 2002

(65) Prior Publication Data
US 2004/0013654 A1    Jan. 22, 2004

Related U.S. Application Data

(60) Provisional application No. 60/239,698, filed on Oct. 12, 2000.

(51) Int. Cl.
C12N 15/02 (2006.01)
C12N 15/88 (2006.01)
A61K 9/127 (2006.01)

(52) U.S. Cl. .................... 435/449; 435/458; 424/450

(58) Field of Classification Search .................... None
See application file for complete search history.

(56) References Cited

U.S. PATENT DOCUMENTS 5,756,352 A * 5/1998 Sridhar et al. ............. 435/375
5,821,354 A * 10/1998 Leclerc et al. ............. 536/24.5
5,908,777 A    6/1999 Lee et al.
5,925,517 A    7/1999 Tyagi et al.
6,110,490 A    8/2000 Thierry
6,506,559 B1 * 1/2003 Fire et al. .................... 435/6

FOREIGN PATENT DOCUMENTS

EP    1 059 092 A1    12/2000
WO    WO/95/24649 A    9/1995
WO    WO 00/14278    3/2000

OTHER PUBLICATIONS

The Merriam Webster's Collegiate Dictionary, 10th edition, 1997, p. 1314.*
Patolsky et al. "Electrochemical Transduction of Lipsome-Amplified DNA Sensing" Angewandte Chemie. Int. Ed. 2000, vol. 39, No. 5, pp. 940-943.
Barthel, F., et al., Laboratory Methods Gene Transfer Optimization with Lipospermine-Coated DNA, DNA Cell Biol. (1993), 12, 553-560.
Feero et al., Selection and use of ligands for receptor-mediated gene delivery to myogenic cells, Gene Therapy, (1997), vol. 4, pp. 664-674.
Felgner, et al. , Lipofection: A highly efficient, lipid-mediated DNA-transfection procedure, Proc. Natl. Acad. Sci. (1987) vol. 84; 9413-7414.
Lee et al, Folgate-targeted, Anionic Liposome-entrapped Polylysine-condensed DNA for Tumor Cell-specific Gene Transfer, J. Biol. Chem., (1996) vol. 271, pp. 8481-8487.
Zhu, N., et al., Systemic Gene Expression After Intravenous DNA Delivery into Adult Mice, Science 261 (1993), 209-211.
Jaschke et al. "Synthesis and properties of oligodeoxyribonucleotide-polyethylene glycol conjugates" Nucleic Acids Research, 1994, pp. 4810-4817; vol. 22. No. 22.
MacKellar et al. "Synthesis and physical properties of anti-HIV antisense oligonucleotides bearing terminal lipophilic groups" Nucleic Acids Research, 1992, pp. 3411-3417; vol. 20. No. 13.

* cited by examiner

*Primary Examiner*—Richard Schnizer
(74) *Attorney, Agent, or Firm*—Fish & Richardson P.C.

(57) ABSTRACT

Coalescence of cells or other membrane-bound entities is facilitated by anchoring an outwardly projecting first oligonucleotide in one member and an outwardly projecting second oligonucleotide, complementary to the first, in a second member and incubating under hybridizing conditions. Liposomes may be coalesced with cells to deliver hydrophilic agents thereto, such as DNA probes or drugs. Kits containing complementary oligonucleotides containing hydrophobic anchoring moieties may be used.

14 Claims, 4 Drawing Sheets

OLIGONUCLEOTIDE-FACILITATED COALESCENCE

This application claims the benefit under 35 U.S.C. Section 119(e) of U.S. Provisional No. 60/239,698, filed Oct. 12, 2000.

Research reported in this application was supported by grant no. ES10536 from the National Institutes of Health. The United States Government may have certain rights in the invention.

TECHNICAL FIELD

This invention relates to coalescence or fusion of cells with each other, fusion of liposomes, membrane vesicles or lipidic particles to cells or to each other. This invention also relates to delivery of membrane impermeable compounds such as hydrophilic drugs and stains into cells and tissues.

BACKGROUND

Biological membranes constitute a barrier which most hydrophilic or charged compounds cannot traverse. Encapsulation of these compounds within liposomes followed by the fusion of the liposomes with cellular membranes can be used to deliver these compounds into cells. This process is useful in delivery of drugs and for gene therapy.

Also due to their membranes, cells stay apart from each other and do not normally fuse. However for a number of applications such as for cloning and generation of hybridomas, it is necessary to fuse two cells with each other. Fusion requires merging of separate membranes into a single membrane structure, and despite efforts to facilitate the fusion with the help of chemical agents and other means such as electric shock, the efficiency of this process is generally poor. This is because the membranes have similar charges on them and thus repel each other, or the hydration shells around the lipid head groups of the membranes interfere with close contact. The two membranes have to be held together for a significant time for fusion to take place, which Brownian motion normally prevents.

An aspect of this invention is a method for improving fusion, or coalescence. of cells liposomes, lipidic particles and lipid bilayer vesicles with cells and with each other by bringing them close to each other and holding them in close proximity so that their membranes can be fused and their contents can be mixed.

Another aspect of this invention is oligonucleotide-coated liposomes containing entrapped substances for delivery into cells.

Another aspect of this invention is reagent kits containing oligonucleotide constructs useful in methods according to the invention.

SUMMARY

The present invention relates to coalescence, or fusion, of membrane-bound entities such as cells, liposomes and lipid bilayer vesicles. "Liposome" as the term is used herein refers to a closed structure comprising an outer lipid bilayer (or multi-layer) member surrounding an internal aqueous space. Examples of synthetic liposomes useful in this invention are cationic lipopolyamines/neutral lipid combinations disclosed in U.S. Pat. No. 6,110,490. Liposomes can be used to package any biologically active agent for delivery to cells. For example, nucleic acids that can be packaged into liposomes for delivery into cells may be oligonucleotide probes, including but not limited to fluorogenic probes such as molecular beacons disclosed in U.S. Pat. No. 5,925,517; antisense agents; ribozymes; interfering RNAs and gene therapy agents such as plasmids and viral vectors. The nucleic acids can be DNA, RNA, PNA and mixtures thereof, and further can contain modified nucleotides and modified internucleotide linkages. Liposomes can also be used to package "cargo" such as therapeutic agents, chemotherapeutic agents, drugs, stains, probes and hydrophilic compounds generally into cells or cellular compartments in vivo or in vitro.

While not containing lipid bilayer membranes surrounding an aqueous internal space, lipidic particles, which are clusters of lipid molecules, can be used in this invention in place of liposomes to transport into cells material with which they complex, notably DNA for transfection, but also proteins, therapeutic agents, chemotherapeutic agents and other nucleic acids. Commercially available lipid mixtures contain, for example N[1-(2,3-dioleyloxy)-propyl]N,N,N-trimethyl-ammonium chloride (DOTMA), dioleylphosphatidyl ethanolamine (DOPE), 2,3-dioleyloxy-N[2-(sperminecarboxamido) ethyl]-N,N-dimethyl-1-propanaminium trifluoracetate (DOSPA), dimethyldioctadecylammonium chloride (DDAB) and 1-2-dioleyloxy-3 (trimethylammonia) propane (DOTAP). Use of lipidic particles to deliver DNA into cells is known, e.g., Fergner, P. L., et al., Proc. Natl. Acad. Sci. USA 84, 7413–7417 (1987); Barthel, F., et al., DNA Cell Biol. 12, 533–560 (1993); and Zhu, N., et al., Science 261, 209–211 (1993).

In order for fusion to take place either in vivo or in vitro between cells or between liposomes (or lipid particles) and cells, the membrane-bound entities must first be brought into contact with one another. This requires energy, because the entities are typically hydrated or even similarly charged. For that reason fusion tends to be inefficient.

According to this invention nucleic acid hybridization is used to force the membrane-bound entities together, facilitating fusion. This is achieved by adding to each membrane-bound entity an oligonucleotide that has an ability to anchor into the membrane. Such oligonucleotides can be constructed by linking a hydophobic moiety, such as cholesterol, at their end. The membrane-anchoring moiety embeds itself within the hydrophobic region of the membrane, leaving the oligonucleotide exposed as a projection extending outwardly from the surface. The oligonucleotides projecting from the first entity (for example, a cell or a liposome) are designed to be complementary to the oligonucleotides projecting from the second entity (for example, a cell or a liposome), and hybridization of the oligonucleotides forces the two entities together. In order to achieve great intimacy in the contact of the two membranes, it is preferred that the membrane-anchoring moiety is linked to the 3' end of one oligonucleotide and to the 5' end of the other oligonucleotide. This distal ends of these complementary oligonucleotides serve to ensnare each other. This initial contact is followed by the annealing of the two oligonucleotides, which draws the two entities together. Formation of the hybrid between the first pair of oligonucleotides makes it easy for the formation of hybrids between other pairs, since they become more accessible. As the two membranes are fluidic in nature, a large number of oligonucleotides rush in to the site of contact between two membranes where they can pair with their complement. The two membranes are held extremely close to each other as multiple pairs of oligonucleotides act as "stitches" between them. Finally the two membranes fuse with each other and the contents of one membrane-bound entity mix with the contents of the other membrane-bound entity.

The facilitator oligonucleotides should be at least five nucleotides in length, preferably at least twenty-five nucleotides in length. They can be deoxyribonucleic acid (DNA), ribonucleic acid (RNA), peptide nucleic acid (PNA) or mixtures thereof. They can include modified nucleotides. They can include modified internucleotide linkages, such as phosphorothioates, phosphoroamidates, or phosphonates.

The membrane-anchoring moiety is a hydrophobic moiety that can readily dissolve in the hydrophobic core of the membrane, for example, cholesterol, a fatty acid, a hydrophobic peptide, ergosterol or a lipid.

The efficiency of fusion between two membrane-bound entities can be increased by utilizing what we refer to as a "hemifusion destabilizer," by which we mean an agent that promotes proceeding from the intermediate state of hemifusion to the state of complete fusion. The hemifusion destabilizer may be a membrane-anchoring moiety which is sufficiently long that it spans both layers of the bilayer membrane. Such entities will allow membrane fusion to proceed faster from the state of hemifusion (a state in which outer layers of the membrane bilayers fuse with each other while the inner layers remain separate) to the state of complete fusion. Membrane-anchoring moieties that span both layers of membrane destabilize the intermediate hemifusion state. Examples of membrane-anchoring moieties that are long enough to span both layers of membranes are the 55-carbon long lipid isoprenoid undecaprenol, the transmembrane segments of membrane proteins, and multimers of cholesterol.

Another approach to destabilize the intermediate state of hemifusion and to promote complete fusion is to use a separate hemifusion destabilizing agent, for example, cone-shaped amphiphilic molecules that preferentially partition in the inner layer of the bilayer membranes as opposed to the outer layer. For example, the membrane-permeable cationic amphiphilic molecule chlorpromazine is a useful agent that will promote fusion in membrane bound entities that have been brought together by oligonucleotides. These separate agents can simply be added to the medium of fusion reactions.

Because hybridization is specific, targeted fusion is enabled. Certain cells in a population of cells can be provided with projecting oligonucleotides which will hybridize with complementary oligonucleotides present on the liposomes. A combination of liposomes with a variety of different oligonucleotides can be used together to target different cells in a population that are tagged with different complementary oligonucleotides. The oligonucleotide may include a cell-specific moiety such as a monoclonal antibody in addition to a membrane-anchoring moiety. Alternatively, a cell-specific anchoring moiety can be used for targeting, for example, ergosterol, which is specific for fungal cells such as yeast. These approaches permit selective fusion of the liposomes with particular cells, for example, tumor cells. Multiple parallel fusions can be carried out in a given population, as cells or liposomes can find "targets" that are provided with the complementary projecting oligonucleotides.

Fusion aids may be utilized in methods according to this invention, either following or simultaneously with hybridization. Several fusion aids are well known, including osmotic shock, electric shock and addition of calcium ions.

This invention also includes liposomes containing projecting oligonucleotides as products. Such products preferably include a hydrophilic cargo, for example, a drug or a DNA probe, as discussed earlier. Additionally, this invention includes kits for transforming liposomes and cells, comprising at least one pair of complementary oligonucleotides, each including an attached cholesterol or other membrane-anchoring moiety.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

Figure 1:
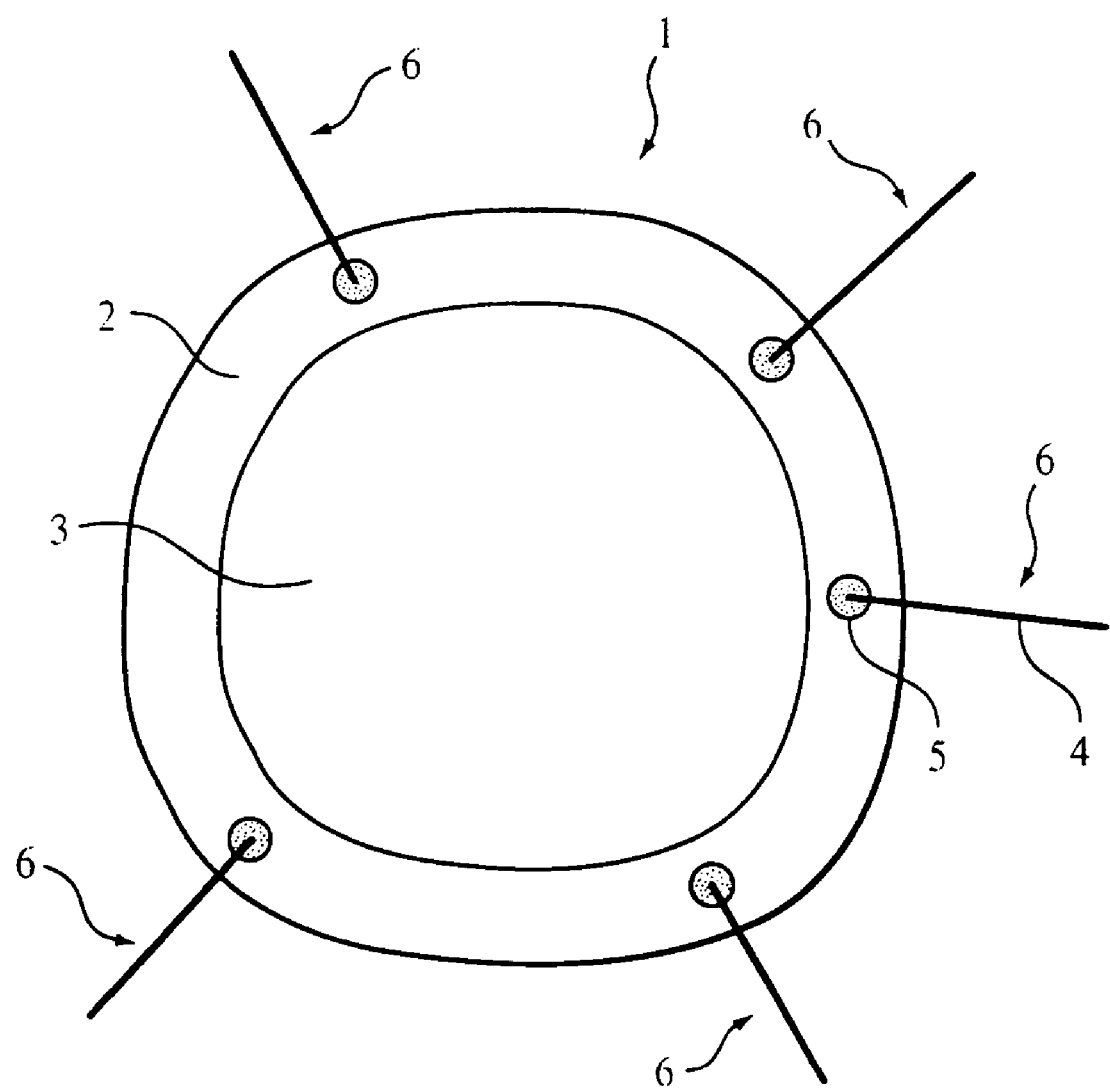
FIG. 1 is a schematic representation of a membrane-bound entity, such as a cell or liposome, containing copies of an anchored oligonucleotide.

FIG. 1 depicts schematically a membrane-bound entity according to this invention. Entity 1, which may be a cell, liposome or lipid bilayer vesicle, comprises membrane or lipid bilayer 2 enclosing a hydrophilic volume or cargo space 3. Entity 1 includes multiple copies of anchored oligonucleotide 6, which contains membrane-anchoring moiety 5 terminally attached to oligonucleotide 4. Membrane-anchoring moiety 5 is embedded in the hydrophobic region of lipid bilayer 2. Oligonucleotide 4 projects outwardly from the membrane. Because of the affinity of membrane-anchoring moiety 5, for example cholesterol, for the hydrophobic region of membrane 2, entity 1 can be prepared simply by incubating oligonucleotide 6 with the membrane-bound entity.

Figure 2:
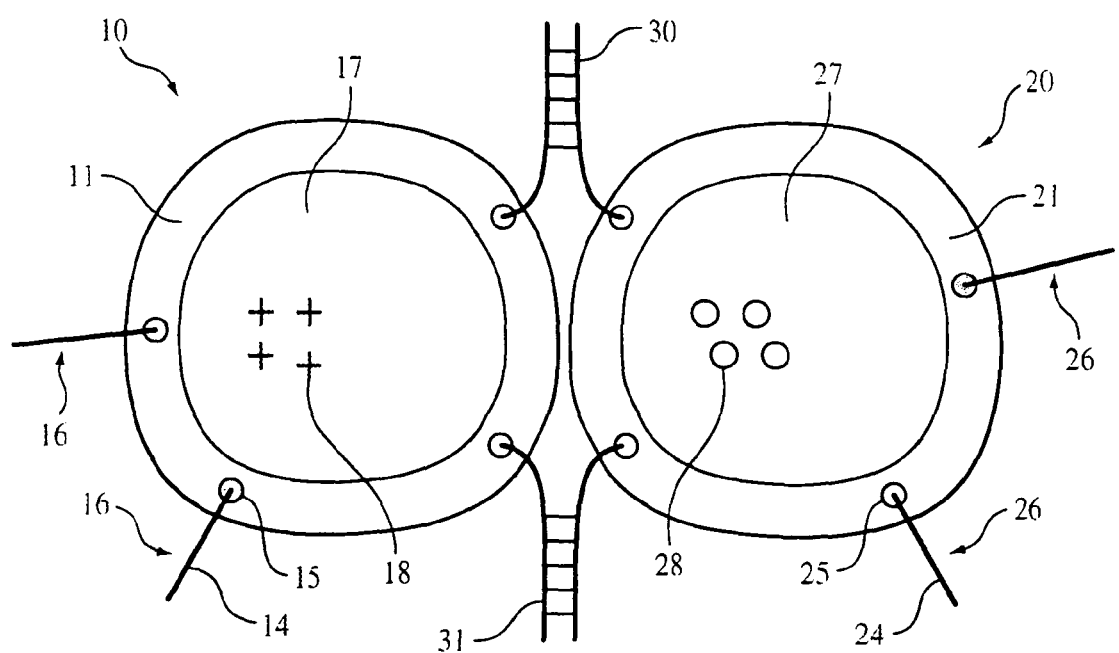
FIG. 2 is a schematic representation of two membrane-bound entities containing copies of complementary anchored oligonucleotides, which have begun to hybridize.

FIG. 2 depicts schematically hybridization according to this invention. Membrane bound entity 10, enclosing hydrophilic volume or cargo space 17 containing hydrophilic cargo 18, comprises membrane 11 and includes multiple copies of anchored oligonucleotide 16, each comprising a membrane anchoring moiety 15 and a projecting oligonucleotide 14. Membrane bound entity 20, enclosing hydrophilic volume or cargo space 27 containing hydrophilic cargo 28, comprises membrane 21 and includes multiple copies of anchored oligonucleotide 26, each comprising a membrane anchoring moiety 25 and a projecting oligonucleotide 24. Projecting oligonucleotides 14 and 24 are complementary to one another. They hybridize to one another to form hybrids 30, 31. In the preferred construction, shown in FIG. 2, one projecting oligonucleotide has a projecting 3' end, and the other has a projecting 5' end. With this construction hybridization can commence at the projecting ends and progress through branch migration toward the membrane-anchoring moieties, thereby pulling entities 10, 20 toward one another. The strength of hybrids 30, 31 can be adjusted as needed to facilitate fusion by changing the length and nucleotide content of the anchored oligonucleotides 16, 26, as will be readily understood.

Figure 3:
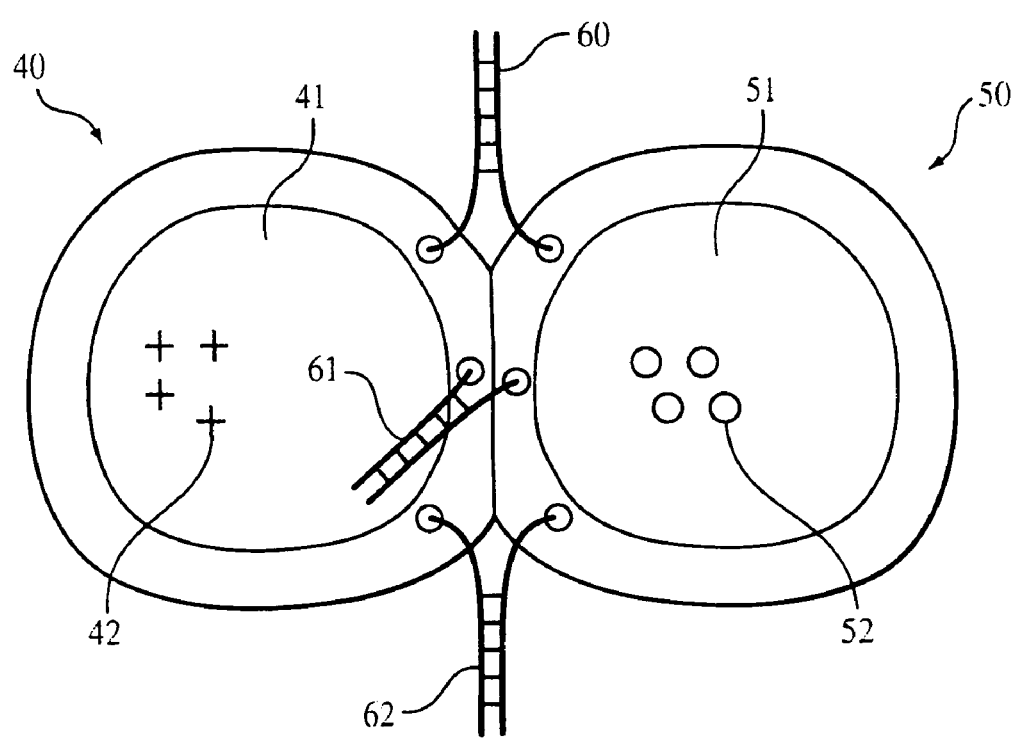
FIG. 3 is a schematic representation of two membrane-bound entities containing copies of complementary anchored oligonucleotides after hybridization has progressed and anchored oligonucleotides have migrated to the area of contact.

FIG. 3 depicts schematically the effect of hybridization in facilitating coalescence. We have observed that anchored oligonucleotides are mobile within the membrane or lipid bilayer. As hybridization proceeds, anchored oligonucleotides migrate toward the area of contact, and the two membrane-bound entities assume a "dumbbell-shaped" overall form with a ring of hybrids surrounding their juncture. Referring to FIG. 3, there is depicted membrane-bound entities 40, 50 containing cargo spaces 41, 51 and cargoes 42, 52. Entities 40, 50 are pulled together by hybrids 60, 61, 62 of their anchored oligonucleotides (see FIG. 2). Together, entities 40, 50 have a "dumbbell" shape, with a narrowed central portion where they meet and are pulled together by the hybrids. By fluorescently labeling one of the anchored oligonucleotides, we have observed the formation of a fluorescent ring around the narrowed portion and a diminution of fluorescence in other areas, showing that anchored oligonucleotides have migrated to the junction area. Microscopic examination show that the two membranes are very close to one another.

Figure 4:
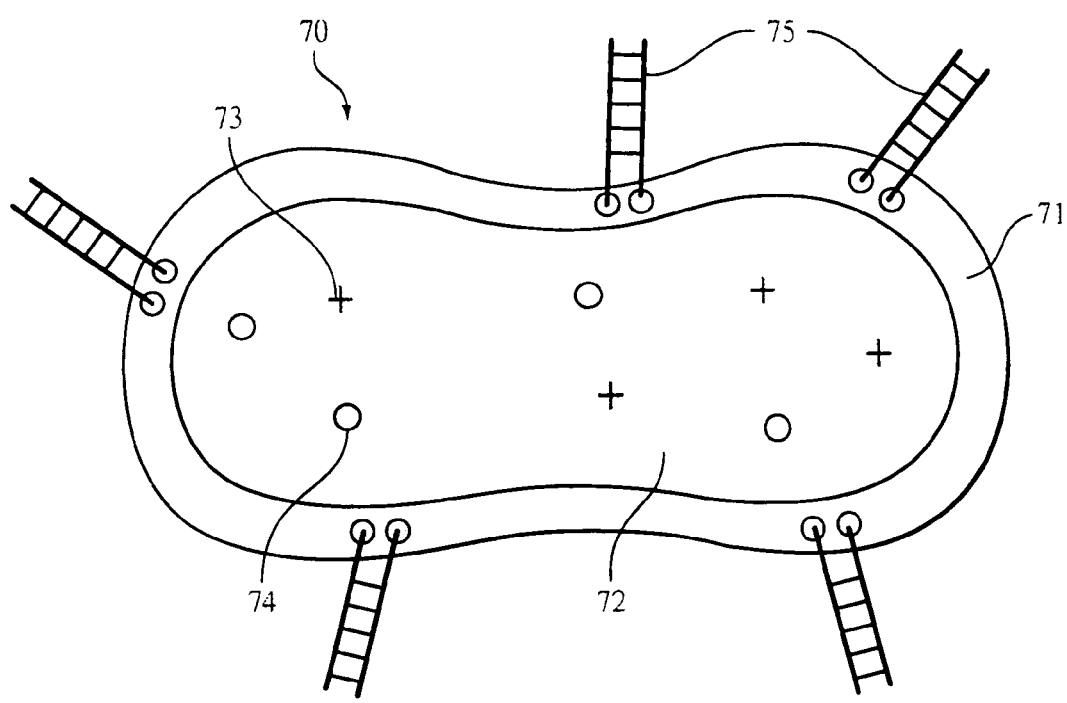
FIG. 4 is a schematic representation of the product of fusion of two membrane bound entities after the two membranes have fused to create one membrane, the paired oligonucleotides are dispersed and the contents of the entities are mixed.

FIG. 4 shows that state of two fused entities after their membranes and the contents are fused to each other. Fused entity 70 comprises a single, fused membrane 71 surrounding a single cargo space 72. Cargo 73 from one parent entity and cargo 74 from the other parent entity (see FIG. 3) are now mixed together in cargo space 72. Hybrids 75 are now free to migrate throughout membrane 71.

The state depicted in FIG. 3 can last for a short or a long time depending upon how unstable the natural state of the two entities are. Liposomes are thermodynamically unstable due to the tension caused by their high surface-to-volume ratios, whereas cells are more stable. Therefore, the state depicted in FIG. 3 lasts longer when two cells pair with each other whereas liposomes readily fuse with cells to which they are bound to via oligonucleotide facilitators. Paired cells also fuse readily when they are osmotically swelled or electrically disturbed. After fusion is complete, the paired oligonucleotides, or hybrids, leave the equatorial plane and disperse homogeneously throughout the membrane as shown in FIG. 4.

Fusion of two membrane-bound entities results in formation of a single spherically shaped structure (circular appearing under a microscope) with projecting hybrids comprising both types of anchored oligonucleotides, as can be shown by fluorescent labeling of the oligonucleotides.

EXAMPLE 1

A pair of complementary anchored oligonucleotides is prepared. The first comprises a DNA oligonucleotide 68 nucleotides in length. Cholesterol is attached to its 5' terminus, and its 3' terminus is labeled with fluoroscein. The second comprises a DNA oligonucleotide 74 nucleotides in length. Cholesterol is attached to its 3' terminus, and its 5' terminus is labeled with tetramethylrhodamine. Its first 68 nucleotides from the 3' terminus are complementary to the first anchored oligonucleotide. When the two nucleotides hybridize to one another, there is a 6-nucleotide overhang separating the two fluorophores. This overhang allows monitoring of the distance between them by measuring resonance energy transfer from fluorescein to rhodamine.

Each cholesterol-containing oligonucleotide is added to a separate suspension of THP1 cells. Five nanograms of each oligonucleotide is added to 10 microliters of a cell suspension. This mixture contains approximately 100,000 cells in cell culture medium (RPMI 1640 medium). The mixtures are incubated for 10 minutes at room temperature. Excess oligonucleotide is removed by flooding the mixture three times with 100 microliters of cell culture medium, spinning down the cells to a 20 microliter volume, and removing the supernatant.

The mixture containing the fluorescein-labeled oligonucleotide is placed on a microscope slide, excited by light at 491 nm wavelength, and the image is recorded at 515 nm. The cells have the appearance of FIG. 1 with a surrounding circle of green fluorescence. Similarly, the mixture containing the tetramethylrhodamine-labeled oligonucleotide is placed on a microscope slide, excited by light at 555 nm wavelength and imaged at 575 nm. These cells have a similar appearance except the color of fluorescence is red.

The two cell suspensions are then mixed and incubated together for 10 minutes at room temperature. The mixture is placed on a microscope slide, and the images are recorded at 491 nm excitation and 515 emission, at 555 nm excitation and 575 nm emission, and at 491 excitation and 575 emission. The first image shows only the fluorescein-labeled cells, which are seen not to pair with each other. The second image shows only the tetramethylrhodamine-labeled cells, which are also seen not to pair with each other. The third image shows only the energy transfer from fluorescein to tetramethylrhodamine at the junction of red and green cells. Numerous dumbbell-shaped composites are observed with energy transfer fluorescence concentrated at the junction between cells, as depicted in FIG. 3. These results confirm that the DNA projections bring the cells that are provided with complementary oligonucleotides together and hold them in close proximity.

EXAMPLE 2

The procedure of Example 1 is repeated with cells whose nuclei are stained (blue) with DAPI. In this example the tetramethylrhodamine label is omitted. Following incubation of the mixture of cell suspensions, the mixture is osmotically shocked by diluting it tenfold with distilled water. After a 10-minute incubation at room temperature, the diluted mixture is spun down to 20 microliters, the supernatant is removed, and the remaining suspension is permitted to stand for one hour. The mixture is then placed on a microscope slide and examined. Many cells with two nuclei are observed and no dumbbell shaped pairs are seen. When the sample is excited with 491 nm wavelength light, and the emission at 515 nm is read, the cells with two nuclei are observed to have the shape shown in FIG. 1 with a ring of fluorescence around them. This experiment shows that two membrane-bound entities that are brought together via DNA facilitators readily fuse when they are under tension.

EXAMPLE 3

Liposomes are prepared by mixing 1-palmitoyl-2-oleoyl-sn-glycero-3-phosphocholile (POPC) and 1,2-dioleoyl-sn-glycero-3-(phospho-L-serine) (DOPS) at a ratio of 85:15. The lipids as purchased are in chloroform. They are mixed and dried with argon gas at the bottom of two glass tubes. The lipids of the first tube are hydrated in presence of an oligonucleotide that contains a fluorescein moiety as its 3' end and the lipids of the second tube are hydrated in the presence of an oligonucleotide that is complementary to the first one and contains a DABCYL moiety at its 3' end. The labeled oligonucleotides represent the cargoes 18, 28 of FIG. 2 or cargoes 42, 52 of FIG. 3. They are designed so that content mixing can be monitored by decrease in fluorescence that accompanies their hybridization. The mixtures are sonicated, producing liposomes containing entrapped oligonucleotides. In order to ensure that the liposomes are of uniform size they are repeatedly passaged through a filtration membrane of 50 nm pore size.

To liposomes of the first tube are added a first cholesterol-containing anchored oligonucleotide, as in Example 1. To liposomes of the second tube are added a complementary second cholesterol-containing anchored oligonucleotide, also as in Example 1. Neither of these oligonucleotides contains any fluorescent label. Uncomplexed oligonucleotides and lipid molecules are removed by gel exclusion chromatography. In parallel, control liposomes that do not contain any facilitator oligonucleotides but do contain the internally entrapped oligonucleotides are retained.

Two mixtures are then prepared: a control mixture containing both liposomes with entrapped oligonucleotides but not facilitator oligonucleotides, and a mixture containing both liposomes having entrapped oligonucleotides and facilitator oligonucleotides. The mixtures are placed in a fluorometer, excited at 491 nm and read at 515 nm. The emission level of the control mixture stays relatively constant over the time, but the emission level of the other mixture drops dramatically over time due to hybridization of the entrapped oligonucleotides and resultant quenching and coalescence. This experiment shows that facilitator oligonucleotides catalyze the fusion of liposomes and mixing of their contents.

What is claimed is:

1. A method for fusing a first cell with a member selected from the group consisting of a second cell, lipid bilayer vesicles and liposomes, comprising:
    (a) incorporating into the plasma bilayer membrane of said first cell an outwardly projecting first anchored oligonucleotide containing a first hydrophobic anchoring moiety attached to the 5' or 3' terminus of the first oligonucleotide,
    (b) incorporating into the bilayer membrane of said member an outwardly projecting second anchored nucleotide, complementary to said first anchored nucleotide, containing a second hydrophobic anchoring moiety attached to the 3' or 5' terminus of the second oligonucleotide,
    (c) mixing said first cell and said member under conditions promoting hybridization of said first and second outwardly projecting anchored oligonucleotides, and
    (d) incubating the mixture of said first cell and said member under conditions producing fusion thereof.

2. The method according to claim 1, wherein the conditions of step (d) include a fusion aid.

3. The method according to claim 1, wherein the member is a liposome containing an entrapped hydrophilic substance to be inserted into said first cell.

4. The method according to claim 3, wherein said hydrophilic substance is selected from the group consisting of DNA, drugs, therapeutic agents, chemotherapeutic agents, antisense agents, stains and oligonucleotide probes.

5. The method according to claim 1, wherein each of the first and second terminal hydrophobic anchoring moieties is selected from the group consisting of cholesterol, a fatty acid, a hydrophobic peptide and a lipid.

6. The method according to claim 1, wherein at least one of said first and second terminal hydrophobic anchoring moieties is a hemifusion destabilizer.

7. The method according to claim 1, wherein said incubation is carried out in the presence of a hemifusion destabilizing agent.

8. The method according to claim 2, wherein said first and second members are cells.

9. The method according to claim 2 wherein the fusion aid is selected from the group consisting of osmotic shock, electric shock, and the addition of calcium ions.

10. The method according to claim 6 wherein said at least one anchoring moiety spans both bilayer membrane layers.

11. The method according to claim 10 wherein both said first and second anchoring moieties span both bilayer membrane layers.

12. The method according to claim 6, wherein the conditions of step (d) include a fusion aid.

13. The method according to claim 1, wherein the member is a liposome, and wherein the second hydrophobic anchoring moiety is a hemifusion destabilizer that spans both bilayer membrane layers.

14. The method according to claim 13 wherein the conditions permitting fusion are the conditions promoting hybridization.

* * * * *